United States Patent [19]

Zeeh et al.

[11] 4,328,236
[45] May 4, 1982

[54] ISOXAZOLYL CARBOXANILIDES, AND THEIR USE FOR COMBATING FUNGI

[75] Inventors: Bernd Zeeh, Ludwigshafen; Hans Theobald, Limburgerhof; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 188,681

[22] Filed: Sep. 19, 1980

[30] Foreign Application Priority Data

Oct. 4, 1979 [DE] Fed. Rep. of Germany ....... 2940189

[51] Int. Cl.³ .................... A01N 43/80; C07D 261/12
[52] U.S. Cl. .................................... 424/272; 548/248
[58] Field of Search .......................... 548/248; 424/272

[56] References Cited

U.S. PATENT DOCUMENTS 4,087,535  5/1978  Heubach ............................ 548/248

FOREIGN PATENT DOCUMENTS 2513732 10/1975 Fed. Rep. of Germany .
2513788 10/1975 Fed. Rep. of Germany .
1448810  9/1976 United Kingdom .
1498199  1/1978 United Kingdom .

*Primary Examiner*—Anton H. Sutto
*Attorney, Agent, or Firm*—Keil & Witherspoon

[57] ABSTRACT

New isoxazolylcarboxanilides of the formula

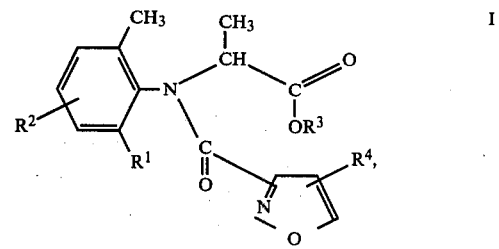

where $R^1$ is methyl, ethyl or chlorine, $R^2$ is hydrogen, methyl, ethyl, fluorine, chlorine or bromine, $R^3$ is methyl or ethyl, and $R^4$ is hydrogen, methyl or ethyl.

These compounds have a fungicidal action and are suitable for combating fungi.

5 Claims, No Drawings

ISOXAZOLYL CARBOXANILIDES, AND THEIR USE FOR COMBATING FUNGI

The present invention relates to new isoxazolylcarboxanilides, processes for their manufacture, fungicides containing these compounds as active ingredients, and methods of combating fungi.

Heterocyclic carboxanilides which are fungicidally effective have been disclosed (German Laid-Open Applications DE-OS No. 2,513,732 and DE-OS No. 2,513,788). Heterocyclic radicals in these compounds are pyridyl, pyrimidinyl, dihydro-pyranyl, dihydro-1,4-thiinyl, thienyl and furyl. The action of these compounds on mildews is unsatisfactory.

We have now found that 1,2-isoxazolylcarboxanilides of the formula

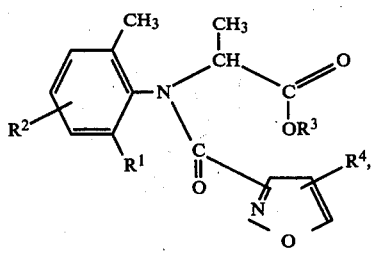

where $R^1$ is methyl, ethyl or chlorine, $R^2$ is hydrogen, methyl, ethyl, fluorine, chlorine or bromine, $R^3$ is methyl or ethyl, and $R^4$ is hydrogen, methyl or ethyl, have an excellent fungicidal action which is superior to that of prior art heterocyclic carboxanilides, particularly on mildews.

The isoxazolylcarboxanilides of the formula I possess a center of asymmetry in the propionic acid ester radical. The optically pure enantiomorphs may be obtained by conventional methods. Not only mixtures (which are usually obtained on synthesis) but also the pure enantiomorphs (which are also encompassed by the invention) are fungicidally effective.

The isoxazolylcarboxanilides of the formula I may be obtained by reaction of an aniline derivative of the formula

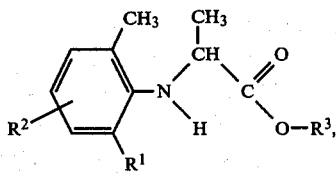

where $R^1$, $R^2$ and $R^3$ have the above meanings, with an isoxazolylcarboxylic acid derivative of the formula

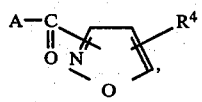

where $R^4$ denotes hydrogen, methyl or ethyl and A denotes a nucleophilically displaceable leaving group, in the presence or absence of a solvent or diluent, in the presence or absence of inorganic or organic bases, and in the presence or absence of a reaction accelerator, at from 0° to 120° C.

Examples of meanings for A in formula III are halogen, such as chlorine and bromine, alkoxycarbonyloxy radicals, such as methoxycarbonyloxy and ethoxycarbonyloxy, benzyloxycarbonyloxy, or an azolyl radical, such as imidazolyl or triazolyl.

The reaction may be carried out in the presence of a solvent or diluent. Examples of preferred solvents or diluents are halohydrocarbons, e.g., methylene chloride, chloroform, 1,2-dichloroethane and chlorobenzene; aliphatic or aromatic hydrocarbons, such as cyclohexane, petroleum ether, benzene, toluene and xylenes; esters, such as ethyl acetate; nitriles, such as acetonitrile; sulfoxides, such as dimethyl sulfoxide; ketones, such as acetone or methyl ethyl ketone; ethers, such as diethyl ether, tetrahydrofuran or dioxane; or mixtures of these solvents.

The solvent or diluent is advantageously employed in an amount of 100 to 2,000 wt%, preferably 100 to 1,000 wt%, based on the starting materials of the formula II or III.

Examples of suitable inorganic or organic bases which may if desired be added to the reaction mixture as acid-binding agents are alkali metal carbonates, such as potassium or sodium carbonate; alkali metal hydrides, such as sodium hydride; tertiary amines, such as trimethylamine, triethylamine, N,N-dimethylanilide, N-N-dimethylcyclohexylamine, N-methylpiperidine and pyridine; and azoles, such as 1,2,4-triazole or imidazole. Other conventionally used bases may, however, also be employed.

Suitable reaction accelerators are preferably metal halides, such as sodium bromide or potassium iodide, azoles, such as imidazoles or 1,2,4-triazole, or pyridines, such as 4-dimethylaminopyridine, or mixtures of these substances. Advantageously, from 0.9 to 1.3 moles of acid derivative of the formula III and, if desired, from 0.5 to 2 moles of base, and, if desired, from 0.01 to 0.1 mole of reaction accelerator are employed per mole of aniline derivative of the formula III.

The reaction is generally carried out at from 0° to 120° C., over a period of from 1 to 60 hours, at atmospheric or superatmospheric pressure, and continuously or batchwise.

In a preferred embodiment of the process according to the invention, the acid derivative of the formula III, and, if desired, the reaction accelerator, are added to the starting material of the formula II which is if desired in admixture with a base and if desired in admixture with a diluent, and the reaction mixture is kept for from 0.5 to 12, preferably from 1 to 6, hours at the reaction temperature which may be from 0° to 120° C.

To isolate the new compounds, the diluent—if any is used—is removed, the residue is dissolved in a suitable solvent and this solution is washed first with dilute acid, then with dilute aqueous alkaline solution and with water to remove excess base and unreacted starting materials II and III.

The products remaining after the solvent has been distilled off do not in general need any further purification, but may if necessary be further purified by conventional methods, such as recrystallization, extraction or chromatography.

The aniline derivatives of the formula II and processes for their manufacture are disclosed in German Laid-Open Application DE-OS No. 2,802,211, J. Org. Chem., 30, 4101–4104, 1965, and Tetrahedron, 487–493, 1967.

Some of the isoxazolylcarboxylic acid derivatives of the formula III used as starting materials are known or may be prepared by conventional methods from isoxazolylcarboxylic acids of the formula

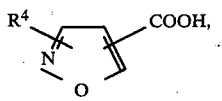

where $R^4$ denotes hydrogen, methyl or methyl.

Some of the carboxylic acids of the formula IV are known (Gazz. chim. ital., 72, 458–474, 1942, ibid., 73, 764–768), 1948) or may be prepared by oxidation of prior art carbinols (Gazz. chim. ital., 69, 536–539, 1939).

The manufacture of isoxazolylcarboxylic acids of the formula IV from the corresponding carbinols by oxidation is illustrated below with reference to 3-ethylisoxazolyl-5-carboxylic acid.

At 15° to 20° C., a mixture of 750 ml of water, 164 g of $Na_2Cr_2O_7.2H_2O$ and 124 ml of sulfuric acid is dripped into 63.5 g of of 3-ethyl-5-hydroxymethylisoxazole in 250 ml of diethyl ether. After the mixture has been stirred for 12 hours at 20° C. to 25° C., the organic phase is separated and dried over sodium sulfate. After removal of the solvent there is obtained 59 g of 3-ethylisoxazolyl-5-carboxylic acid of melting point 194° C.

| | $C_6H_7NO_3$ (141) | | |
|---|---|---|---|
| | C | H | N |
| calc.: | 51.1 | 5.0 | 9.9 |
| found: | 51.9 | 5.2 | 10.7 |

The following table contains the melting points of some carboxylic acids of the formula IV:

| | COOH | IV |
|---|---|---|

| $R^4$ | Position of the COOH group on the isoxazole ring | M.p. (°C.) |
|---|---|---|
| H | 3 | 149 |
| H | 4 | 123 |
| H | 5 | 144 |
| 5-$CH_3$ | 3 | 176 |
| 3-$CH_3$ | 5 | 211 |

The following example illustrate the manufacture of isoxazolylcarboxanilides of the formula I. Parts by weight bear the same relationship to parts by volume as kilograms to liters.

EXAMPLE 15.2 parts by volume of triethylamine and then a solution of 16 parts by weight of 3-methylisoxazolyl-5-carboxylic acid chloride in 30 parts by volume of toluene are dripped into a solution of 20.7 parts by weight of N-(1-methoxycarbonylethyl)-2',6'-dimethylaniline in 100 parts by volume of toluene, the temperature of the reaction mixture rising to 64° C. After the mixture has been stirred for 2 hours at room temperature, 50 parts by volume of water is added. The organic phase is separated, washed 3 times, each time with 50 parts by volume of water, dried and concentrated. The oil which remains is distilled under reduced pressure.

At 0.005 mbar and 170°–174° C., there is obtained 24.1 parts by weight of 3-methylisoxazolyl-5-carboxylic acid-N-(1'-methoxycarbonylethyl)-(2'',6''-dimethyl)-anilide (active ingredient No. 1).

| | $C_{17}H_{20}O_4N_2$ (316.3) | | |
|---|---|---|---|
| | C | H | N |
| calc.: | 64.5 | 6.4 | 8.9 |
| found: | 64.6 | 6.3 | 8.9 |

For instance the following compounds of the formula I may be prepared analogously:

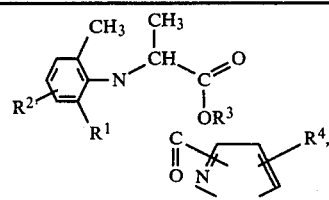

| No. | $R^1$ | $R^2$ | $R^3$ | $R^4$ | Position of the CO group on the isoxazole ring | Physical data |
|---|---|---|---|---|---|---|
| 2 | $CH_3$ | H | $CH_3$ | 3-$C_2H_5$ | 5 | b.p. 170–174° C./0.01 mbar |
| 3 | $CH_3$ | H | $C_2H_5$ | 3-$C_2H_5$ | 5 | oil |
| 4 | $CH_3$ | H | $CH_3$ | H | 3 | b.p. 75–77° C. |
| 5 | Cl | H | $CH_3$ | H | 3 | b.p. 85° C. |
| 6 | $CH_3$ | 3-$CH_3$ | $CH_3$ | H | 3 | oil |
| 7 | $CH_3$ | 4-Br | $CH_3$ | H | 3 | b.p. 85° C. |
| 8 | $CH_3$ | H | $CH_3$ | H | 4 | |
| 9 | Cl | H | $CH_3$ | H | 4 | |
| 10 | $CH_3$ | 3-$CH_3$ | $CH_3$ | H | 4 | |
| 11 | $CH_3$ | 3-$CH_3$ | $CH_3$ | H | 5 | $n_D^{20}$ 1.5310 |
| 12 | Cl | H | $CH_3$ | H | 5 | m.p. 108–110° C. |
| 13 | $CH_3$ | H | $CH_3$ | H | 5 | m.p. 88–90° C. |
| 14 | $C_2H_5$ | H | $CH_3$ | 3-$CH_3$ | 5 | $n_D^{20}$ 1.5250 |
| 15 | $C_2H_5$ | H | $CH_3$ | H | 3 | $n_D^{20}$ 1.526 |

The active ingredients according to the invention have a strong fungitoxic action. At the concentrations necessary for combating fungi and bacteria, they cause no damage to crop plants. For these reasons they are suitable for use as crop protection agents for fighting fungi.

The new active ingredients have a strong fungitoxic action on phytopathogenic fungi. The new compounds are suitable for instance for combating *Erysiphe graminis* in cereals, *Erysiphe cichoriacearum* in Cucurbitaceae, *Erysiphe polygoni* in beans, *Phytophthora infestans* in tomatoes and potatoes, *Phytophthora parasitica* in strawberries, *Podosphaera leucotrichia* and *Phytophthora cyctorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in grapes, *Plasmopara halstedii* in sunflowers, *Sclerospora macrospora* in Indian corn, *Bremia lactucae* in lettuce, *Mucor mucedo* in fruit, *Rhizopus nigricans* in beets, *Uncinula necator* in grapes, and *Sphaerotheca pannosa* in roses.

The application rates depend on the type of effect desired and are from 0.1 to 5 kg of active ingredient per hectare. Some of the active ingredients have curative properties, i.e., the agents may also be applied after the plants have been infected by the pathogen, and success is still ensured. Furthermore, many of the new compounds have a systemic action, which means that visible plant parts may also be protected by a root treatment.

The new compounds may also be used to combat fungi which cause seedling and emergence diseases, e.g., Pythium and Aphanomyces species in Leguminosae and cotton. For this use, the active ingredients are applied as seed disinfects at rates of from 10 to 200 g of active ingredient per 100 kg of seed.

The compounds are applied by spraying or dusting the plants with the active ingredients or treating the seed with the active ingredients. Treatment may be effected before or after the plants or seed have been infected by the fungi.

The active ingredients of the invention can be converted into the conventional formulations, e.g. solutions, emulsions, suspensions, dusts, powders, pastes, and granules. The forms of application depend entirely on the purpose for which the agents is to be used; at all events, it should ensure a fine and uniform distribution of the active ingredient. The formulations are prepared in the conventional manner, for example by diluting the active ingredient with solents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.p. petroleum fractions, alcohols, e.g. methanol and butanol, amines, e.g. ethanolamine and dimethylformamide, and water; carriers for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents contain from 0.1 to 95, and preferably from 0.5 to 90, wt% of active ingredient.

The formulations, and the ready-to-use preparations obtained therefrom, e.g., solutions, emulsions, suspensions, powders, dusts, pastes or granules, are applied in the conventional manner, e.g. by spraying, atomizing, dusting, treating seed, or watering.

Examples of such formulations are given below.

I. 90 parts by weight of compound 1 is mixed with 10 parts by weight of N-methyl-α-pyrrolidone. A mixture is obtained which is suitable for application in the form of very fine drops.

II. 20 parts by weight of compound 1 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound 4 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound 5 is well mixed with 3 parts by weight of the sodium salt of diisobutyl-naphthalene-α-sulfonic acid, 17 parts by weight of sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 3 is intimately mixed with 97 parts by weight of particulate kaolin. A dust is obtained containing 3% by weight of the active ingredient.

VII. 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 2 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

IX. 20 parts of compound 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients according to the invention may be mixed and applied with other active ingredients, e.g., herbicides, insecticides, growth regulators and other fungicides or may be mixed with fertilizers and applied together with these. Mixture with other fungicides often broadens the spectrum of fungicidal action.

The following list of fungicides with which the compounds according to the invention may be combined is intended to illustrate and not restrict the combination possibilities. Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenyl-hydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thiouredio)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, diisopropyl 5-nitroisophthalate, 1-(1',2',4'-triazol-1'-yl)-[1-(4'-chlorophenoxy)]-3,3-dimethylbutan-2-one, 1-(1',2',4'-triazol-1'-yl)-[1-(4'-chlorophenoxy)]-3,3-dimethylbutan-2-ol, N-(n-propyl)-N-(2,4,6-trichlorophenoxyethyl)-N'-imidazolylurea, N-cyclohexyl-N-methoxy-2,5-dimethylfuran-3-carboxamide, 2,4,5-trimethylfuran-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, and N-[3-(p-tert-butylphenyl)-2-methylpropyl]-cis-2,6-dimethylmorpholine.

The following examples demonstrate the biological action of the new compounds of the formula I. The agents used for comparison purposes were the fungicidal compounds N-(1'-methoxycarbonylethyl)-N-(furan-(2")-carbonyl)-2,6-dimethylaniline (A; German Laid-Open Application DE-OS No. 2,513,788) and N-(1'-methoxycarbonylethyl)-N-(pyridine-3"-carbonyl)-2-methyl-6-chloroaniline (B; German Laid-Open Application DE-OS No. 2,513,732).

EXAMPLE A

Action on wheat mildew

Leaves of pot-grown wheat seedlings of the "Jubilar" variety are sprayed with aqueous emulsions containing of 80% (by weight) of active ingredient and 20% of emulsifier, and dusted, after the sprayed-on layer has dried, with spores of wheat mildew (*Erysiphe graminus* var. *tritici*). The plants are then placed in a greenhouse at 20° to 22° C. and 75 to 80% relative humidity. The extent of mildew spread is determined after 10 days.

| spraying with liquor containing Active ingredient | Leaf attack after active ingredient in amounts of | | | |
|---|---|---|---|---|
| | 0.05% | 0.025% | 0.012% | 0.006% |
| 1 | 0 | 2 | 2–3 | 4 |
| 2 | 0 | 1 | 2 | 2–3 |
| 3 | 0 | 0 | 2 | 2–3 |
| 4 | 0 | 0 | 1 | 2 |
| Comparative agent A | 5 | 5 | — | — |
| Comparative agent B | 4 | 5 | 5 | 5 |
| Control (untreated) | 5 | | | |

0 = no fungus attack, graduated down to
5 = total attack

EXAMPLE B

Fungicidal action on *Phytophthora infestans* in tomatoes

Leaves of tomato plants of the "Professor Rudloff" variety are sprayed with aqueous suspensions containing (dry basis) 80% (wt%) of active ingredient and 20% of sodium lignin sulfonate. 0.1, 0.05, 0.025 and 0.012% (dry basis) spray liquors are used. After the sprayed-layer has dried, the leaves are infected with a zoospore suspension of *Phytophthora infestans*. The plants are then placed for 5 days in a steam-saturated (moist) chamber kept at 16° to 18° C. After this period, the disease has spread on the untreated control plants to such an extent that the fungicidal action of the compounds can be assessed.

| Active ingredient | Leaf attack after spraying with liquor containing active ingredient in amounts of | | | |
|---|---|---|---|---|
| | 0.1% | 0.05% | 0.025% | 0.012% |
| 1 | 0 | 1 | 2 | 2 |
| 4 | 0 | 0 | 0 | 2 |
| 5 | 0 | 0 | 1 | 1 |
| 6 | 0 | 0 | 0 | 0 |
| 13 | 0 | 0 | 0 | 1 |
| Comparative agent A | 1 | 2 | 3–4 | 4 |
| Comparative agent B | 2 | 3 | 4 | 4 |
| Control (untreated) | 5 | | | |

0 = no fungus attack, graduated down to
5 = total attack

EXAMPLE C

Fungicidal action on *Plasmopara viticola* in grapes

Leaves of potted vines of the Müller-Thurgau variety are sprayed with aqueous suspensions containing (dry basis) 80% (by weight) of the active ingredient and 20% of emulsifier. 0.05% and 0.012% spray liquors (dry basis) are used. To assess the duration of action of the active ingredients, the plants are placed after the sprayed-on layer has dried, for 10 days in the greenhouse. Only then are the leaves infected with a zoospore suspension of *Plasmopara viticola*. The plants are then placed for 16 hours in a steam-saturated (moist) chamber at 24° C. and then for 8 days in a greenhouse at from 20° to 30° C. To accelerate and intensify the sporangiophore discharge, the plants are then again placed in the in the moist chamber for 16 hours. Fungus attack is then assessed on the undersides of the leaves.

| Active ingredient | Leaf attack after spraying with liquor containing active ingredients in amounts of | |
| --- | --- | --- |
| | 0.025% | 0.012% |
| 1 | 0 | 0 |
| 2 | 0 | 0 |
| Control (untreated) | 5 | |

0 = no attack, graduated down to

5 = total attack

We claim:

1. An isoxazolylcarboxanilide of the formula

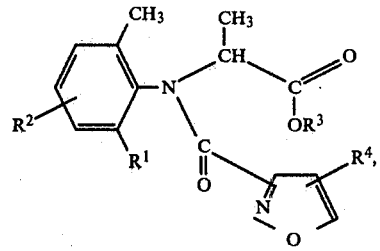

where $R^1$ is methyl, ethyl or chlorine, $R^2$ is hydrogen, methyl, ethyl, fluorine, chlorine or bromine, $R^3$ is methyl or ethyl, and $R^4$ is hydrogen, methyl or ethyl, with the proviso that where $R^4$ is other than hydrogen, the isoxazole is 3,5-disubstituted.

2. Isoxazolyl-3-carboxylic acid-N-(1'-methoxycarbonylethyl)-(2'',6''-dimethyl)-anilide.

3. 3-Methylisoxazolyl-5-carboxylic acid-N-(1'-methoxycarbonylethyl)-(2'',6''-dimethyl)-anilide.

4. A fungicidal agent comprising at least one isoxazolylcarboxanilide of the formula I as claimed in claim 1 and a solid or liquid carrier.

5. A process for combating fungi, wherein at least one isoxazolylcarboxanilide of the formula I as claimed in claim 1 is allowed to act on the fungi, or on areas, plants or seed threatened by fungus attack.

* * * * *